United States Patent
Clement et al.

(10) Patent No.: US 8,248,249 B2
(45) Date of Patent: *Aug. 21, 2012

(54) SELF-POWERED RFID TAG ACTIVATED BY A FLUID

(75) Inventors: Jean-Yves Clement, Saint Jeannet (FR); Pierre Secondo, Tourrettes sur Loup (FR); Jerome Tarte, La Gaude (FR)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/343,093

(22) Filed: Jan. 4, 2012

(65) Prior Publication Data

US 2012/0119915 A1    May 17, 2012

Related U.S. Application Data

(63) Continuation of application No. 12/443,722, filed on Mar. 31, 2009.

(30) Foreign Application Priority Data

Oct. 30, 2006  (EP) ..................................... 06301099
May 28, 2007  (WO) ................. PCT/EP2007/055144

(51) Int. Cl.
  *G08B 23/00*  (2006.01)
(52) U.S. Cl. ................. 340/573.5; 340/10.1; 340/572.1; 340/573.1
(58) Field of Classification Search .................. 340/505, 340/573.1, 573.5
See application file for complete search history.

(56) References Cited

U.S. PATENT DOCUMENTS

| | | | | |
|---|---|---|---|---|
| 8,057,454 B2 * | 11/2011 | Long et al. | ............... | 604/385.26 |
| 2005/0099294 A1 * | 5/2005 | Bogner et al. | ................ | 340/540 |
| 2008/0266117 A1 * | 10/2008 | Song et al. | ................ | 340/573.5 |
| 2009/0315720 A1 * | 12/2009 | Clement et al. | ............ | 340/573.5 |

OTHER PUBLICATIONS

Ki Bang Lee, Urine-Activated Paper Batteries, PowerMEMS 2004, Nov. 28-30, 2004, Kyoto, Japan, pp. 108-111.

* cited by examiner

*Primary Examiner* — Travis Hunnings
(74) *Attorney, Agent, or Firm* — Hoffman Warnick LLC; Andrea Bauer (57) ABSTRACT

RFID tag and a system and method involving a plurality of RFID tags. Each RFID tag is attached to an object on which the presence of a predefined fluid is monitored. In a first state, (absence of the monitored fluid), the tag acts as a passive RFID tag, and the information it holds can be read with a proximity reader. This operation is performed when the RFID tag is attached to the object to be monitored. In a second state, whenever the monitored fluid appears on the tagged object, a fluid activated battery generates the electrical power which is used to power the RFID tag. The RFID tag then acts as an active RFID tag and starts to emit messages which can be received by a RFID reader.

20 Claims, 8 Drawing Sheets

| | OBJECT NAME | OBJECT LOCATION | Pointer to associated file | Additional Information |
|---|---|---|---|---|
| TAG ID 1 | | | | |
| TAG ID 2 | | | | |
| ..... | | | | |
| TAG ID n | | | | |

SELF-POWERED RFID TAG ACTIVATED BY A FLUID

CROSS-REFERENCE TO RELATED APPLICATIONS

This application is a continuation application of co-pending patent application Ser. No. 12/443,722, filed on Mar. 31, 2009, which is incorporated herein by reference in its entirety.

TECHNICAL FIELD

The present invention relates to Radio Frequency Identifier (RFID) tags and more particularly to a passive fluid activated RFID tag that becomes active when it detects a predefined fluid.

RELATED ART

The problem is to monitor the presence of a fluid at one or several different places and to report this information to a distant central site. Many documents of the prior art relate to the detection of the presence of fluid using sensors. Other documents describe the use of passive or active RFID tags on objects to collect information by means of RFID readers. The problem is to find a system:
- capable of detecting a fluid on an object or person in one or different places;
- capable of sending this information and other data to a distant site;
- permanently easily identifiable;
- autonomous in terms of energy;
- easy to build;
- cheap enough to be disposable.

Detection of a Liquid Using Non-Contact Tags

US patent application 2004/0070510 entitled "Radio frequency wetness detection system" discloses a detection system used in, e.g. diaper for detecting the presence of urine, includes passive resonant tag having substrate, inductor, and capacitor, and a remote detection mechanism having transmitter, alarm, and antenna. A moisture monitoring device is provided having a resonant tag and a remote detector. The resonant tag comprises a plastic substrate having holes punched through it, a capacitor plate on one side that is connected to a second capacitor plate and inductor coils on the other side. The resonant tag comprises a live LC circuit having a natural resonant frequency that does not activate the detector. The resonant tag is affixed to absorbing materials in a diaper or other sanitary undergarment. Upon the introduction of moisture into the circuit, the resonant frequency is eliminated as the circuit is deactivated and an alarm in the detector is triggered. At this point it would be apparent to a parent or caretaker that the diaper is wet and in need of replacement.

In US patent application 2004/0070510 the effect of the liquid detection is to de-tune a resonant circuit. The information provided by this system is a binary information "on" or "off". No data is transmitted by the detector. This prevents the system to automatically discriminate, from a remote location, several systems detecting moisture at the same time.

Japanese patent JP2005000602 entitled "Wet Diaper Informing and Indicating Device and Diaper Equipped with Wet Detecting Device" discloses a system to provide a wet diaper informing device and a diaper equipped with a wet detecting device which allow a care-giver to determine easily whether a user of the diaper is within a tolerable limit when the exchange of the diaper is delayed by informing the wet status of the diaper, such as the number of times the diaper gets wet or the time elapsed since the diaper got wet. The wet diaper informing device and the diaper equipped with wet detecting device comprise a wet detecting device and a display device. The wet detecting device has a radio frequency-identifier (RF-ID) tag comprising an IC chip having a data storing medium for storing the number of times that wet signals are generated or the time elapsed since a wet detecting signal was entered, a printed antenna and a communication control section. A control section transmits data stored in the data storing medium to the communication control section via the antenna. The display device comprises a communication control section, a control section, an antenna and a display section. The display section displays, in response to the transmitted data, the number of times that the wet signals are generated or the time elapsed since the wet detecting signal was entered.

In Japanese patent JP2005000602, the system is not autonomously powered. The wet detector is just providing information to the system, but does not provide any power to the tag that only operates as a passive tag (short distance reading).

Powering of Wetness or Liquid Sensors

US patent U.S. Pat. No. 5,959,535 entitled "Electrogalvanic-powered diaper wetness sensor" Remsburg Ralph, discloses an electrical wetness sensor powered by the electrogalvanic action of an anode, a cathode and an electrolyte. In an embodiment the electrolyte is urine and the device is used to warn of incontinence. This device contains the following features: sensitivity to wetness; electrical battery-less operation; hermetic and permanent sealing; no-maintenance operation; portability, inexpensiveness, and disposableness. The alarm unit may be configured to produce a visual and/or audible signal. In an embodiment the alarm unit transmits a signal to a remote FM radio receiver or dedicated device to announce incontinence. Incontinence is announced by a tone, visual signal, silencing of the radio station the receiver is tuned to, or activation of a microphone within the alarm unit to allow remote listening.

U.S. Pat. No. 5,959,535, does not use an RFID system and therefore, cannot provide means to read the stored data as long as the battery is not in operation. Moreover, for distant operation, U.S. Pat. No. 5,959,535 uses an FM radio signal, which transmits just an alarm. No additional information, like localisation is transmitted. Moreover, adding an FM modulator is expensive.

Japanese patent JP2000329732, Okuyama Yuji, entitled "Excretion detecting device" discloses a detection device that is safe for a user and enables a detection part to be used easily again by using a battery that is solid in a dry state, uses an electrolyte for indicating acidity when being dissolved in water, and generates power when water is added. The detection device for reporting excretion when a person wearing a diaper performs excretion is provided with, for example, a cathode, a dried electrolyte, an anode, and a transmitter. The transmitter and an electric wire are protected from direct urine while being covered, for example, with a resin case. Zinc or magnesium, citric acid, and carbon, copper, silver, or gold can be used as the cathode, an electrolyte, and the anode, respectively. A weak acid other than the citric acid that is solid when it is dry and is not harmful to a human body may be used. Then, when a battery is fitted to a specific position and is exposed to urine, water enters the electrolyte and power is generated and then an electronic wave is emitted from the transmitter. By opening the resin case or the like, the part of the electrolyte and the cathode can be exchanged.

Japanese patent JP61167854 entitled "Liquid sensor" discloses a system to eliminate the need for having a power source device on the outside or in the outside and to obtain a liquid sensor which is small in size, inexpensive and is suitable for a throw-away application by constituting a primary battery of plural electrodes consisting of different materials and electrolyte in a detecting part. The comb-shaped electrodes which constitute a positive electrode and negative electrode are formed of the different materials on a substrate. The electrodes are formed of, for example, carbon for the positive electrode and Ni for the negative electrode. A water absorbent consisting of, for example, PVA powder and starch is formed like a film onto the substrate containing the electrodes. The electrolyte such as $NH_4Cl$ and depolarizer such as $MnO_2$ are mixed with the absorbent. The primary battery is thereby constituted of the electrodes and the detecting part consisting of the absorbent which is a mixture composed of the electrolyte and depolarizer. The primary battery functions when water or urine is adsorbed to the absorbent. Then the electrolytic $NH_4Cl$ induces an ionization reaction and the current flows between the electrodes. The detection circuit is driven by the electromotive force thereof.

Japanese patents JP2000329732, JP61167854 describe only a detection device and liquid sensor powered by a battery activated by a liquid. This detection device or liquid sensor is not based on the RFID technology and cannot transmit in a wireless way to a remote system data (for instance the position) related to tagged objects.

Japanese patent JP4138155 entitled "Urinary Incontinence Detector" discloses a system to suppress the consumption of a power source voltage and enhance the life by assembling an urinary incontinence detecting member by two kinds of different metallic materials producing an electromotive voltage by a potential difference caused by urine to form a pair of metallic terminals, capable of mutually approaching and separating for operating an urinary incontinence detecting circuit on the basis of the electromotive voltage. Metallic terminals are inserted to a determined position of a paper diaper which is worn by a patient, and the remote distance between the metallic terminals is set to a desired value according to an urinary incontinence state such as urine quantity. When the space between the metallic terminals is wetted by urine, a potential difference is caused between them to generate an electromotive voltage, which operates an urinary incontinence detecting circuit to detect the urinary incontinence state, and a light emitting diode is operated to inform the patient itself or a helper of the urinary incontinence state. In this urinary incontinence detector, as a base current for turning ON the urinary incontinence detecting circuit is supplied by the electromotive voltage generated between the metallic terminals the consumption of the power source voltage by a battery can be suppressed, thus enhancing the life.

Japanese patent JP4138155 describes a local system. The care person must be in front of the patient to see the alarm. It does not have a radio system (RFID). This system is not based on a RFID technology which can transmit in a wireless way to a remote system, data (in particular the position) related to tagged objects.

SUMMARY OF THE INVENTION

The present invention provides a RFID tag acting:
in a first state as a passive RFID tag and
in a second state, as a self powered active tag in the presence of a fluid, capable of sending information to a distant RFID reader.

The present invention monitors from a remote central site a plurality of geographically distributed tagged objects and collects information from RFID readers in particular about the presence of a fluid in these tagged objects together with the identification and geographical location of these objects.

The present invention is directed to a RFID tag, to a method for tagging and to a method for monitoring, to a system for carrying out the method for monitoring, to a computer program and to a diaper as defined in independent claims.

The Radio Frequency Identifier (RFID) tag for monitoring a presence of a fluid according to the present invention comprises:

The method according to the present invention for tagging a plurality of geographically distributed objects or individuals with the claimed RFID tag, comprising:

The method in a distant site, for remotely monitoring a plurality of geographically distributed RFID tags according to the present invention, comprises:

Further embodiments of the invention are provided in the appended dependent claims.

The foregoing, together with other objects, features, and advantages of this invention can be better appreciated with reference to the following specification, claims and drawings.

BRIEF DESCRIPTION OF THE DRAWINGS

The new and inventive features believed characteristics of the invention are set forth in the appended claims. The invention itself, however, as well as modes of use, further objects and advantages thereof, will best be understood by reference to the following detailed description of an illustrative detailed embodiment when read in conjunction with the accompanying drawings.

DETAILED DESCRIPTION

The present invention describes a system comprising one or more fluid activated RFID tags. Each tag is attached to an object (or to a structure or a person) on which the presence of a predefined fluid is monitored.

In a first state, (absence of the monitored fluid), the tag is acting as a passive RFID tag, and the information it holds, (at least its identifier—ID), can be read with a proximity reader (a hand held or stationary/fixed reader). This operation is performed when the tag is attached to the object (or person) to be monitored. At this stage a table associating tag ID, object name (or person name) and location (or any other information), may be built, and may be recorded so that information it contains is accessible by a Control Center.

In a second state, whenever the monitored fluid appears on the tagged object, a fluid activated battery generates an electrical power which is used to power the tag. The tag then acts as an active tag and starts to emit messages (an alert for instance) which can be received by a distant RFID reader. Alert messages include at least the tag ID but may comprise additional information like a name or a location.

In a particular embodiment RFID readers, are positioned in such way they can receive messages from several tags in order to monitor (for instance 20 or more) them at the same time within a given area.

In a particular embodiment, RFID readers are wirelessly connected to a remote central site (a Control Center for instance) in order to transmit the messages received from the tags. The Control Center is equipped with processing means and may comprise a monitoring dashboard.

On receipt of an alert message, the Control Center may search in the table with the tag ID as lookup key, for additional information concerning the object, person or location on which the RFID tag is attached. The Control Center may also trigger a visual or sound alarm and displays information related to the alarm on a dashboard of the Control Center, allowing the personal to take appropriate actions.

Figure 4:
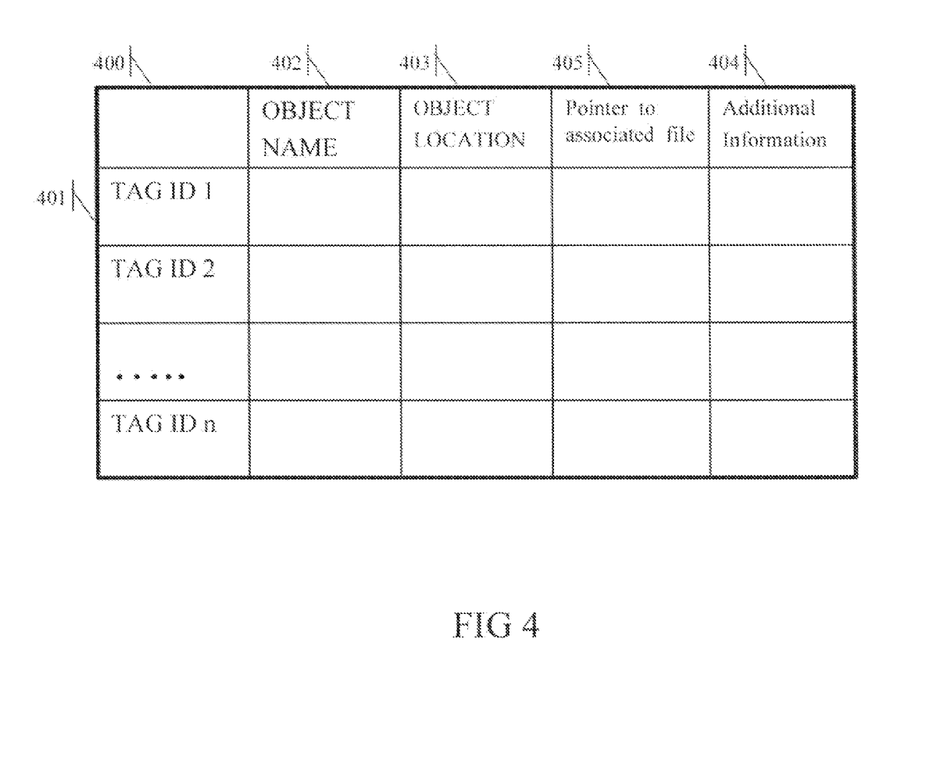
FIG. 4 shows the table according to the present invention, associating with each RFID tag identifier, a name, a location and additional information.

FIG. 4 shows a table (400) according to the present invention, associating with each RFID tag identifier (401) a name (402), a location (403), additional information (404) and optionally a reference to a file or site (405) also containing information concerning the object, person or location.

Fluid Activated RFID Tags

Radio Frequency Identification (RFID) technology is developing very fast and it is used in almost all sectors of the economy in various applications. The basic function of this technology is to allows an RFID tag, attached to an object to transmit, in a wireless way (Radio Frequency), an information to a reader also called interrogator or receiver. In the basic applications, this information is just an "Identification" of the object. Other applications store additional information in the tag. The additional information can be related to the object itself or can also be related to the status or environment of this object. This additional information can be obtained by associating appropriate sensors with the tag.

There are may types of RFID tags, however, they can be classified into two categories:

tags that do not use a battery to operate, called "passive tags", and tags that do use a battery, known as "semi-passive" or "active" tags.

The power delivered by the battery is generally used to allows the tag to operate at a longer distance—several meters for "semi-passive" tags and up to tens or hundreds of meters for "active" tags —, while the passive tags are only operating in a short range—centimeters to few meters.

Most "semi-passive" and "active" tags operate like passive tags. They react (answer) when they are interrogated by a reader by sending the data they hold. The difference between the two being that "semi-passive" tags uses the energy of a battery only to enhance the power of the response signal, while active tags uses the energy of an embedded battery for all operations. Other active tags can send data in a "unsolicited" way, avoiding repetitive polling from an interrogator, and generally to a longer distance.

The present invention, discloses a new kind of fluid activated RFID tag acting as a passive RFID tag, and becoming autonomously powered, and then acting as an active tag in the presence of a specific fluid. The invention combines an electronic tag circuitry with a battery subsystem which, in its initial state, is inactive, and starts to produce electrical power when the specific fluid is present.

The fluid activated RFID tag according to the present invention can be used to monitor water appearance but can also have many other applications like the monitoring of leaks or flood or in the field of agronomy, the monitoring of plants watering. In these embodiments, the fluid activated RFID tag uses a water activated battery.

In another particular embodiment, the fluid activated RFID tag, is inserted in a diaper/undergarment and used to detect incontinence of babies, aged persons or a patients.

Fluid-Activated Batteries

One critical issue to be addressed is the power sources for microsystems especially for autonomous systems which must stay in standby mode during a long period of time.

Urine-Activated Paper Batteries for Biosystems

An example of battery which can be activated by a fluid and which can be embedded in a RFID tag according to the present invention is described in publication entitled "Urine-activated paper batteries for biosystems" (Ki Bang Lee, Institute of Bioengineering and Nanotechnology, 31 Biopolis Way, The Nanos, #06-08, Singapore 138669) J. Micromech. Microeng. 15 (2005) S210-S214 doi:10.1088/0960-1317/15/9/S06. This publication describes a urine-activated laminated paper battery. A simple and cheap fabrication process for the paper batteries is disclosed which is compatible with the existing plastic laminating technologies or plastic molding technologies. In this battery, a magnesium (Mg) layer and copper chloride (CuCl) in the filter paper are used as the anode and the cathode, respectively. A stack consisting of a Mg layer, CuCl-doped filter paper and a copper (Cu) layer sandwiched between two plastic layers is laminated into the paper batteries by passing through the heating roller at 120° C. The paper battery can deliver a power greater than 1.5 mW. In addition, these urine-activated laminated paper batteries could be integrated with bioMEMS devices such as home-based health test kits providing a power source for the electronic circuit.

Figure 1:
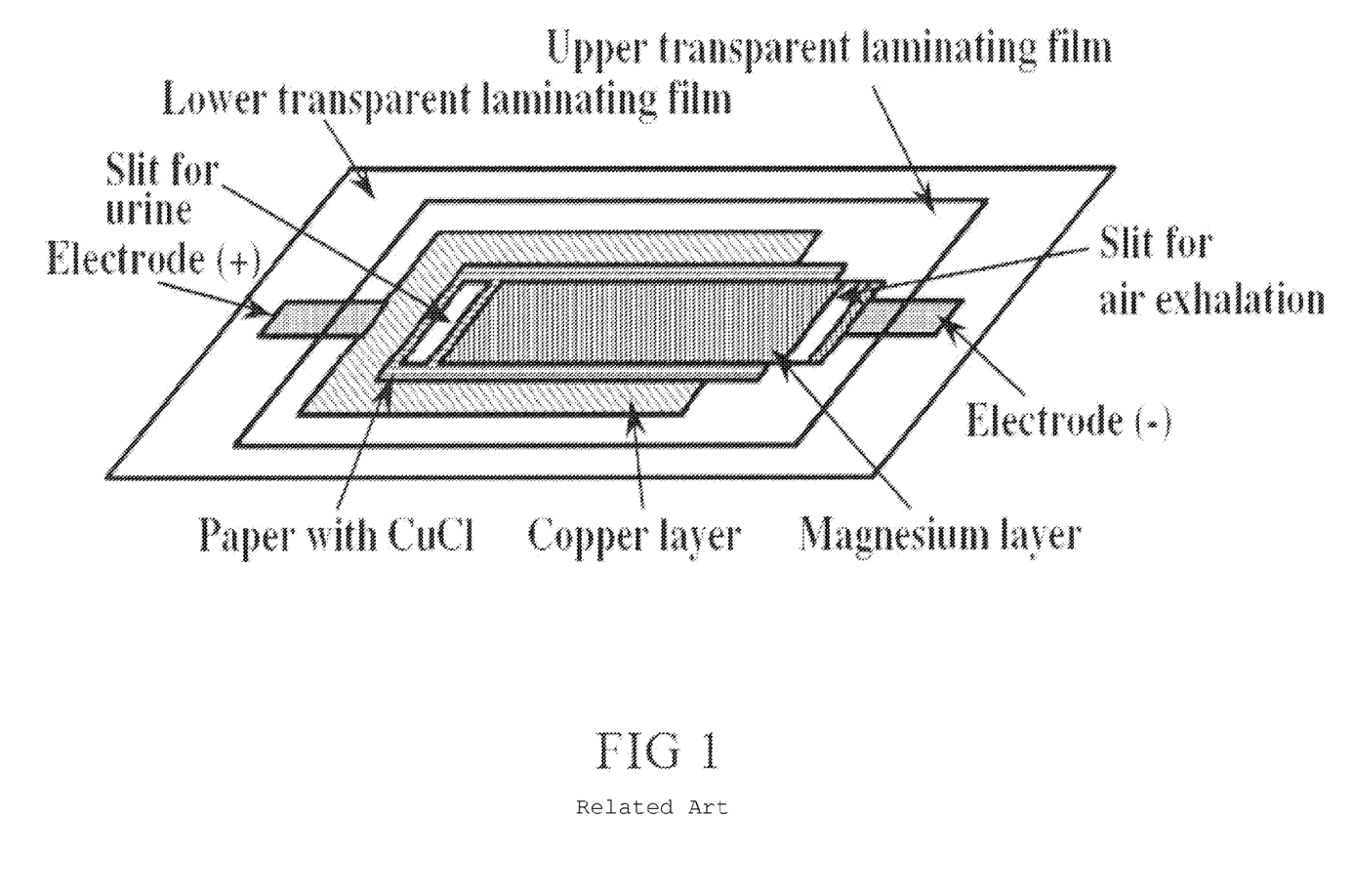
FIG. 1 shows a schematic diagram of a urine-activated paper battery consisting of a copper (Cu) layer, copper chloride (CuCl)-doped filter paper and a magnesium (Mg) layer.
Figure 2:
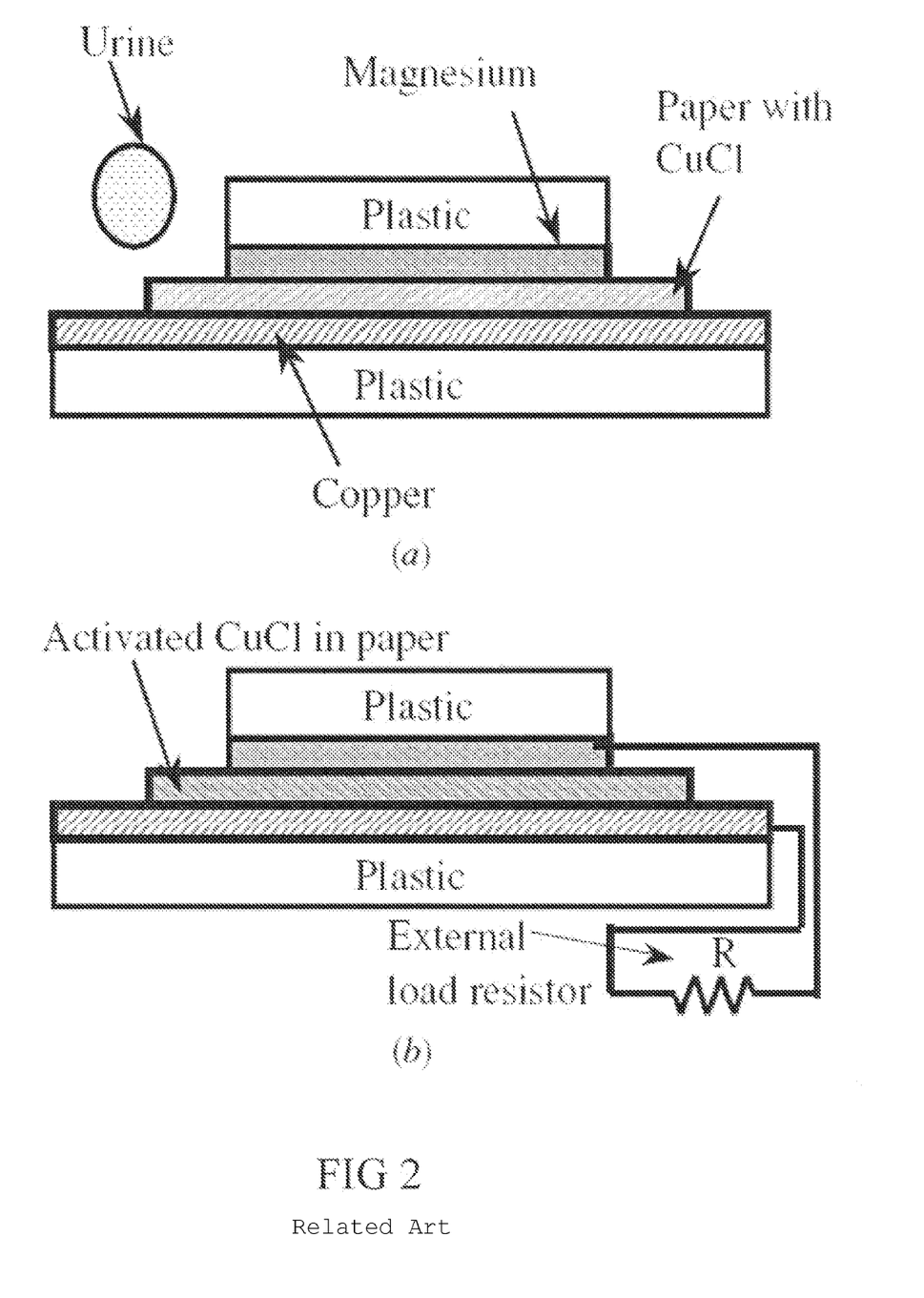
FIG. 2 shows the working principle of the urine-activated paper battery (a) before activation and (b) after activation.

FIG. 1 shows the schematic diagram of a urine-activated paper battery consisting of a copper (Cu) layer, copper chloride (CuCl)-doped filter paper and a magnesium (Mg) layer. The whole assembly is sandwiched between two plastic layers and later laminated into a urine-activated paper battery by passing it through heated rollers at 120° C. FIG. 2 shows the operation principle of the urine-activated battery. Magnesium and copper chloride are used as the anode and the cathode, respectively. The Cu layer acts as an electron-collecting layer. When a droplet of human urine is added to the battery, as shown in FIG. 2, the urine soaks through the paper between the Mg and Cu layers. The chemicals dissolve and react to produce electricity. Even though urine contains other minor electrolyte chemicals such as uric acid, CuCl, as shown in FIG. 2, is the major chemical used for the generation of electric power in these batteries. The chemical reactions for the battery at the anode (oxidation) and cathode (reduction) are represented as equations (1) and 2), respectively:

$$Mg => Mg^{2+} + 2e^- \quad (1)$$

$$2CuCl + 2e^- => 2Cu + 2Cl^- \quad (2)$$

and the overall reaction is $$Mg + 2CuCl => MgCl_2 + 2Cu. \quad (3)$$

The theoretical voltage of this battery is a direct function of the anode and cathode materials. The standard potential can be calculated as 2.49 V from the standard electrode potentials as the sum of the anode potential and the cathode potential.

Water-Activated Paper Batteries

An example of battery which can be water-activated and which can be embedded in a RFID tag according to the present invention is described in U.S. Pat. No. 5,395,707. This patent discloses a primary reserve battery for use in an environment, such as the ocean, that provides an environmentally safe battery, especially useful in sonobuoys. The battery includes the use of cuprous iodide as a cathode and magnesium as the anode in an array to provide voltage, amperage, and operational time equivalent to conventional lead chloride batteries. Once the sonobuoy is no longer useful as it deteriorates in the environment, no lead will be presented into the ocean. The structural frame members protect the cuprous iodide which is brittle in a rigid array and provides for proper venting of gas and sludge formation to insure efficient operation of the battery.

Other kinds of batteries activated by other fluids like water can be found in the literature. For instance, U.S. Pat. No. 4,185,143 discloses a water activated battery using a metal/organo-halogen couple wherein the anode and cathode are formed as planar members with a porous insulator sandwiched between there are provided channels to allow the electrolyte access throughout the cell. The channels may be cut in the cathode or the cathode may be formed as discrete portions of cathode reactant material deposited on a current collector backing plate.

Application in the Field of Health Care

Figure 6:
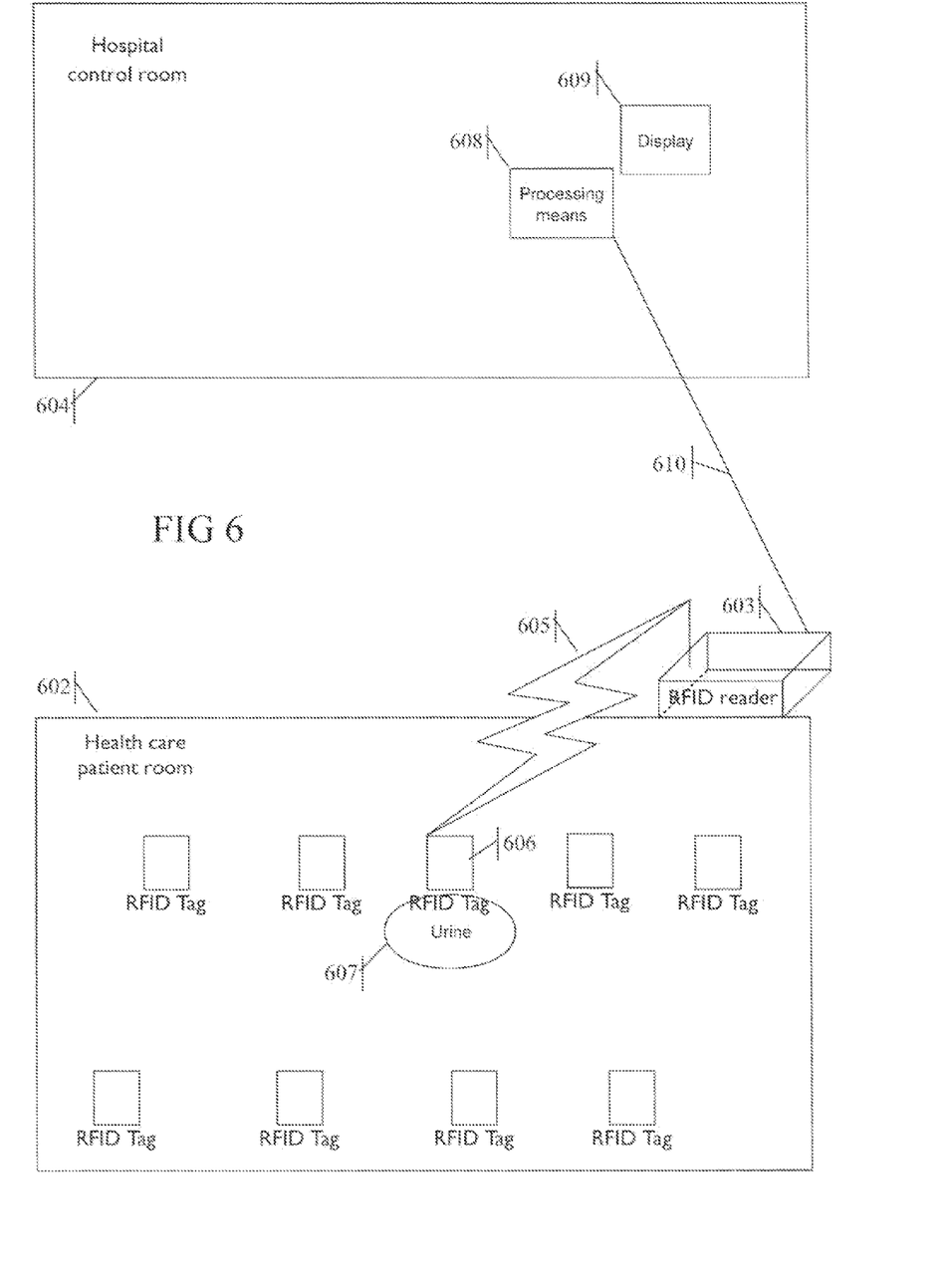
FIG. 6 is a general view of the application of the RFID tag in the field of health care.
Figure 8:
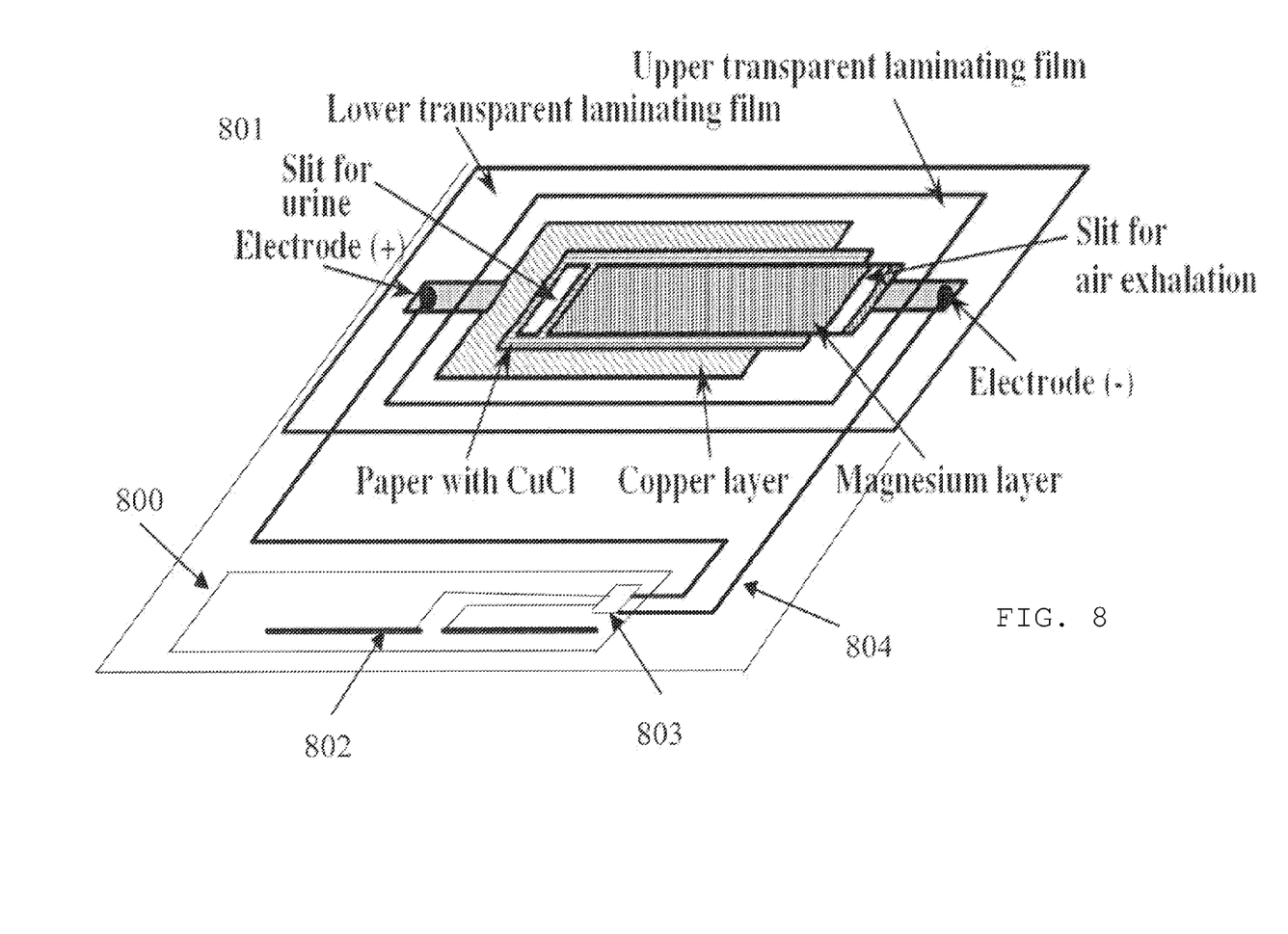
FIG. 8 is a view of a urine activated RFID tag according to the present invention.

The present invention can be used in the field of heath care, in hospitals or nurseries where few care persons have to take care of many patients or babies. An object of the invention is to assist the work of the care persons while delivering a better care to the patients. In the particular embodiment shown in FIG. 6, the RFID system comprises:

- a plurality of urine activated RFID tags (601) placed in the diaper of persons located in a patient room (602). FIG. 8 shows an example of urine activated RFID tag comprising a RFID circuitry (800) connected to the urine activated battery (801) already described in FIGS. 1 and 2. The RFID circuitry comprises a dipole antenna (802), an electronic chip (803) and connections to the urine activated battery (804).
- at least a RFID reader (603). The RFID reader is located in the patient room (602) (or not far from the patient room in a control room (604)). Its role is to detect information (605) transmitted by RFID tags (606) acting as active tags in presence of urine (607) and to transmit (610) said information to processing means (608) in a remote control room (604) (preferably using wireless communication means) and;
- processing means (608) located in the remote control room (604), and
- optionally, a display system (609) connected to the processing means (608).

The purpose of this system is to inform the care personnel that a patient (or a baby in case of a maternity hospital) has wetted his/her undergarment/diaper. The RFID systems identifies and localizes the patient. As in public hospitals (or maternity hospitals), a single nurse takes care of several patients (or babies), sharing a common room or hosted in different rooms, sometimes on different floor, it is essential for the RFID tags to be active when the presence of urine is detected so that they can send an alert to a remote site.

Method for Tagging a Diaper

Figure 3:
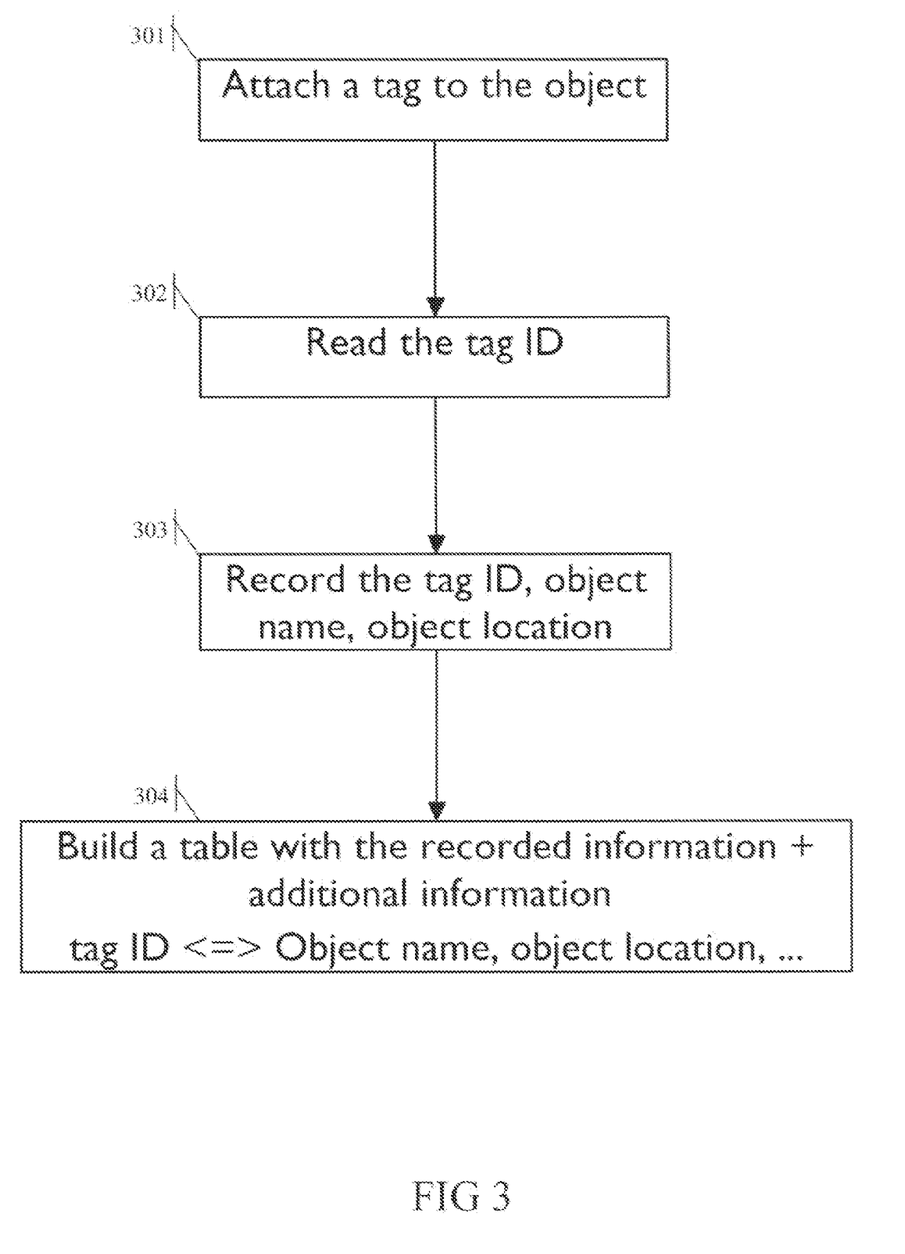
FIG. 3 is a flow chart of the method of attaching tags to objects according to the present invention.

In a first step, as shown in FIG. 3, a urine activated RFID tag according to the present invention, is inserted (301) in the diapers/undergarments of babies, aged persons or a patients to detect incontinence. When an undergarment/diaper is allocated to a person, the nurse first reads (302) with a hand held RFID tag reader the ID of the RFID tag attached to the undergarment/diaper in order to associate the ID of the RFID tag with the person and to the location. The RFID tag ID and associated name and location of the person are recorded (303) and stored (304) in a table (400). Thus, the system can later retrieve from the table the patient/baby name and location associated with this ID when this ID will be read by the RFID reader of the Control Center.

Method for Detecting Urine

As previously described, the RFID tag according to the present embodiment, is first inserted in the undergarment/diaper of a person (a baby or an incontinent person). As long as the undergarment/diaper is dry, the RFID tag is not enabled and acts as a passive RFID tag. No alarm signal can be sent. However, the RFID tag can be read to identify the person wearing the undergarment/diaper. When a biological fluid is detected by the urine activated RFID tag in a diaper/undergarment, the tag begins to be powered and becomes active. It starts emitting information (at least its ID but also in a particular embodiment, its location). A RFID reader receives the information and sends it to the Control Center which displays it on a dashboard of a central monitoring room. Thanks to a search based on the received ID, the patient/baby name and location, and potentially other medical information (like disease, severity, . . . ) can be retrieved from table and appropriate actions can be taken.

Figure 5:
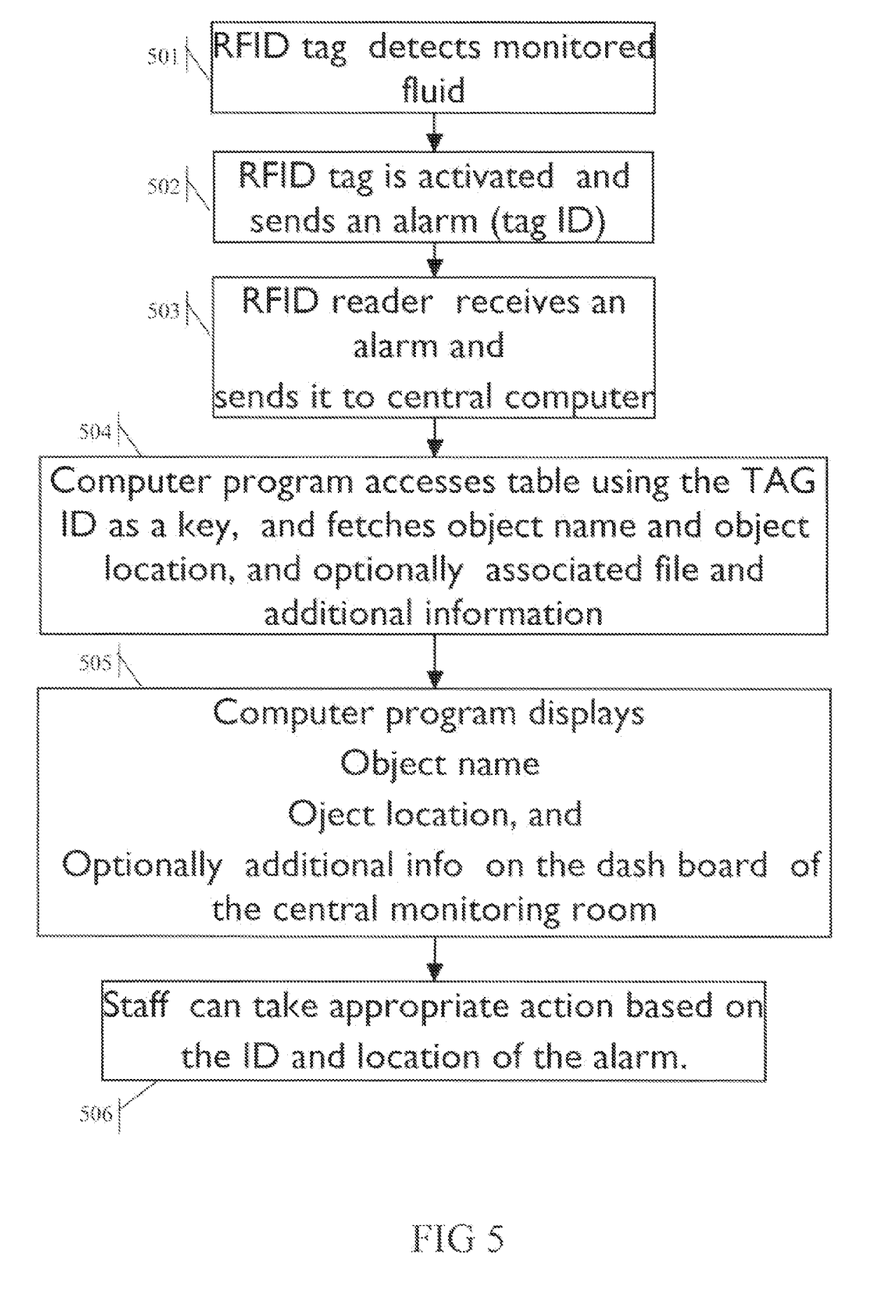
FIG. 5 is a flow chart of the method of detecting urine according to the present invention.

As shown in FIG. 5, the method of detecting urine comprises the following steps:

Step 501: When the person urinates in the undergarment/diaper, the urine creates an electro chemical reaction in the urine-activated battery which produces the electric power required to enable the RFID tag.

Step 502: As soon as the RFID tag is powered, it acts as an active RFID tag and starts to emit an alarm signal, said alarm signal comprising the RFID tag identifier (ID).

Step 503: The signal is detected by an RFID reader.

Step 504: In an embodiment, the name, location and also additional information associated with the received RFID tag identifier (ID) are retrieved from the table previously created.

Step 505: Optionally, the alarm and also information concerning the person (name, location and other information) are displayed on the dashboard (or on any other display) of the central monitoring room.

Step 506: The medical staff knowing the name and the location of the person can take appropriate actions. Various processes can be triggered:

the person wakes up; and an alert is sent to parents (if the baby is at home) or to the nursing staff (if the baby is in a maternity hospital or if the person is in an hospital).

Figure 7:
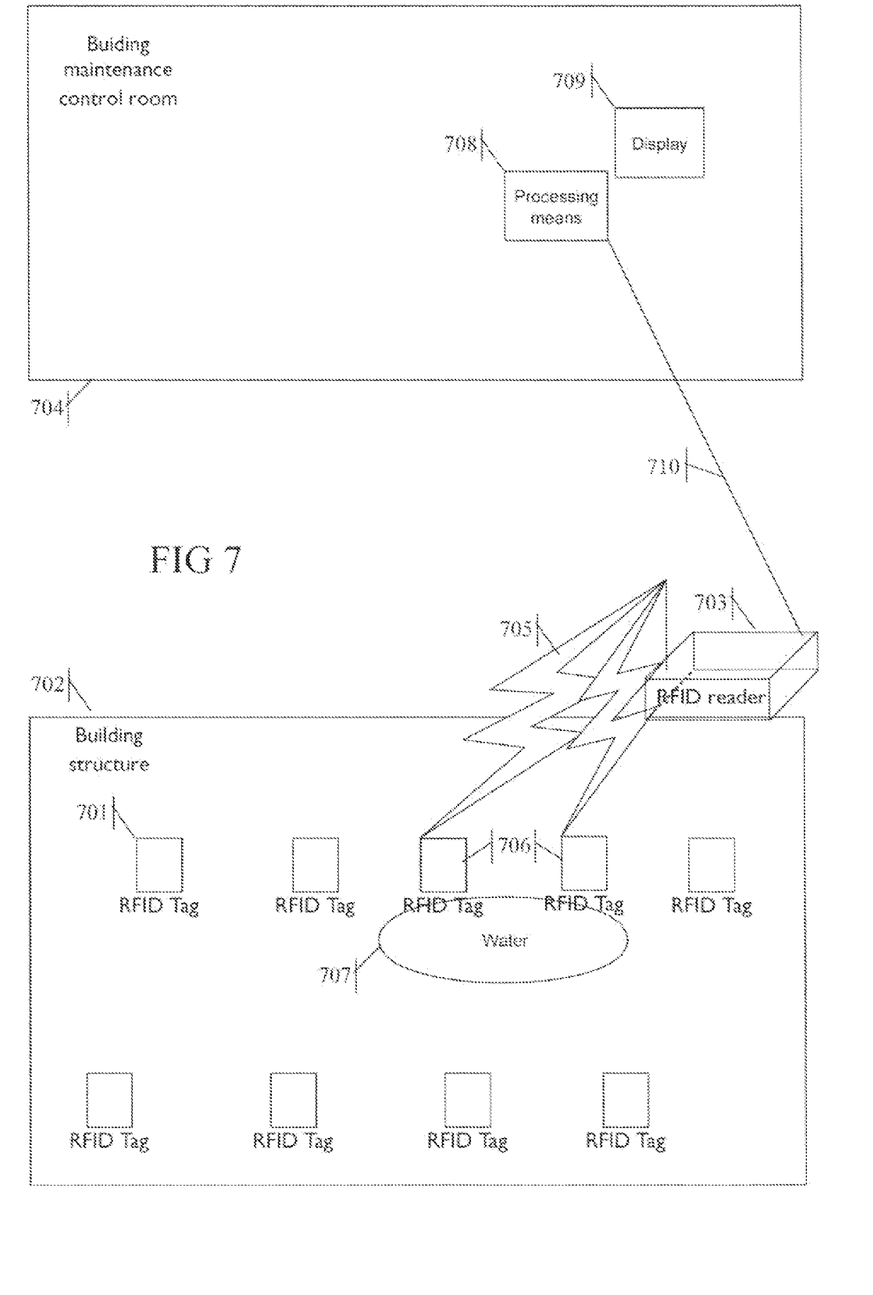
FIG. 7 is a general view of the system for detecting water according to the present invention.

Method for Detecting Leaks of Water The present invention can also be used to localize leaks of water in buildings, dam, boats, tanks, ground or anywhere else. In this particular application, an object of the invention is to assist the work of the persons in charge of the maintenance while delivering a better diagnostic. In this alternate embodiment, the RFID fluid-sensor tag is glued on a structure and or objects. As shown in FIG. 7, the RFID system comprises:

a plurality of tags (701) positioned at different places in the structure (702), at least a RFID reader (703). The RFID reader is located in the structure (or not far from the structure in a control room (704)). Its role is to detect information (705) transmitted by RFID tags (706) acting as active tags in presence of water (707) and to transmit (710) this information to processing means (708) (preferably using wireless communication means);

processing means (708) located in the remote control room (704), and optionally, a display system (709) connected to the processing means (708).

The RFID systems identifies and localizes the leak and determine how this leak evolves. As soon as a leak appears, during a rain fall for example, the first RFID tag detecting water localizes the leak. The second, the third and the other RFID tags detecting the liquid will give a good idea of the way the liquid is flowing. In particular, by correlating the information, it is possible to determine the speed at which the liquid is flowing.

When a structure is completely flooded, it is often impossible for the person in charge of the maintenance to find where the leak come from. In case of periodic or recurrent leaks or flooding, if the RFID tags are correctly positioned before the leak appears (for instance on the structure of a building, on the walls or on the roof), the analysis of the successive detections by the RFID tags allows an easy localization the leaks. It is essential for the RFID tags to be active when the presence of the water is detected so that an alert can be rapidly sent to a remote site.

According to the present invention, a set RFID fluid-sensor tag is positioned in the structure—even in hidden locations—in order to detect water leaks. The field engineer first reads with a hand held RFID tag reader the identifier (ID) of each RFID tag attached to each specific location in order to associate the ID of each RFID tag with its particular location. Thus, the system can later on determine by means of a table or a map the particular location associated with each ID when an ID will be read by the RFID reader of the Control Center.

When a fluid is detected by the fluid activated RFID tag, the tag begins to be powered and becomes active. It starts emitting information (at least its ID but also in a particular embodiment, its location). A RFID reader receives the information and sends it to the Control Center which displays it on a dashboard of a central monitoring room. Thanks to a search based on the received ID, the location can be retrieved from the table and appropriate actions can be taken.

Method of Detecting Water in a Building

In a first step, a RFID tag with a particular RFID identifier (ID) code is associated with each location in the structure. In its initial state, the RFID tag is not powered by the battery and is inactive. The RFID tag can be read with an hand held reader only at a very short distance.

In a second step, when the presence of a fluid on the structure (concrete wall, wood roof framework, tank, boat, ground . . . ), the batteries begin to produce power. Once it is supplied, the RFID tag becomes active and can send an alert to a centralized system (a long distance RFID tag reader). The information is forwarded to a central board which identifies based on the received ID, the location of the RFID tag, and informs the maintenance staff of the situation concerning this particular structure.

A RFID tag is placed in each suspected place within the building. As long as the suspected places are dry, the RFID tags are not enabled and act as passive RFID tags. No alarm signal can be sent. However, the RFID tags can be read to identify the exact location of the suspected places in the building.

The method of detecting water in a building (or in another structure) comprises the following steps:

When the leakage appears, the water creates an electro chemical reaction in the water-activated battery which produces the electric power required to enable a RFID tag. Each RFID tag detecting water acts as an active RFID tag and starts to emit an alarm signal.

The signal is detected by a RFID reader.

The location and also additional information associated with the received RFID tag identifier (ID) are retrieved from the table previously created.

Optionally, the alarm and also additional information concerning the location of the RFID tag is displayed on the dashboard (or on any other display) of the central monitoring room.

Various processes can be triggered:

the emission time is recorded; and an alert is sent to a maintenance center.

The reception of successive signals from RFID tags can be used to measure various parameters such as the speed of the water, the volume of water, the high of the water . . . . In particular, the information associated with said RFID tags can be correlated in order to take appropriate actions.

Advantages

Some of the advantages of the present invention are listed here after:

The RFID system is autonomous: unlike all other "Active" RFID tags, that require a separate power source (battery) for long distance operations, the RFID part of the RFID fluid-sensor tag according to the present invention draws its energy from the associated fluid sensor in order to act as an active tag. The power source is dynamically created when needed "on demand". When no fluid is detected by the sensor, the fluid activated RFID tag still works. It then acts as a passive tag and is able to communicate in short range.

The RFID system is wireless: the communication between the RFID fluid-sensor tag and the reader is wireless. No wire is required between the tag holder and the reader making the system very practical to use.

The RFID system is secure: The system is secure since no high voltage power (outlet) is used to make the RFID tag active and no battery is embedded. A low voltage to make the RFID tag active, (typically lower than 2 Volts) is required for a short period of time (the time necessary to send the ID to the reader).

The RFID system monitors the fluid on real time: The alert is instantaneous: There is virtually no delay between the appearance of the fluid and the alert transmission. This is a real time monitoring sensor.

The RFID system is cheap: fluid activated batteries and RFID tags are cheap and easy to build. They can be disposable.

The RFID system allows long distance—multi-point operations: The system acts as an active RFID tag. The fluid activated RFID tag is capable to send its ID to a reader located at tens of meters. The reader can receive alerts from many tags. In a nursery with many kids in the same room, the system can identify which kid needs to be taken care of.

While the invention has been particularly shown and described with reference to various embodiments, it will be understood that various changes in form and detail may be made therein without departing from the spirit, and scope of the invention.

What is claimed is:

1. An apparatus for monitoring a presence of a fluid, comprising:
a radio frequency identifier (RFID) tag comprising a fluid activated battery for providing electric power to the RFID tag when a fluid is present, wherein the RFID tag is configured to:
act as a passive RFID tag when a fluid is absent; and
act as a self-powered active tag when a fluid is present.

2. The apparatus according to claim 1, wherein the RFID tag stores information, the information comprising:
an RFID identifier and information regarding at least one of a location, a structure, an individual, or an object.

3. The apparatus according to claim 2, wherein the information stored in the RFID tag can be read by an RFID reader when the RFID acts as a passive RFID tag, and
wherein the information stored in the RFID tag can be transmitted to an RFID reader when the RFID tag acts as an active RFID tag.

4. The apparatus according to claim 3, wherein the information that can be read when the RFID tag acts as a passive RFID tag is different from the information that can be transmitted when the RFID tag acts as an active RFID tag.

5. The apparatus according to claim 1, wherein the fluid activated battery comprises a urine activated battery.

6. The apparatus according to claim 1, wherein the RFID tag monitors a presence of urine.

7. The apparatus according to claim 1, wherein the RFID tag is attached to a diaper.

8. The apparatus according to claim 1, wherein the fluid activated battery is a water activated battery.

9. The apparatus according to claim 1, wherein the RFID tag monitors a presence of water.

10. The apparatus of claim 1, wherein the RFID tag monitors fluid leakage in a structure or object.

11. An apparatus, comprising:
a diaper; and
a radio frequency identifier (RFID) tag comprising a fluid activated battery for providing electric power to the RFID tag when a fluid is present in the diaper, wherein the RFID tag is configured to:
act as a passive RFID tag when a fluid is absent; and
act as a self-powered active tag when a fluid is present.

12. The apparatus of claim 11, wherein the fluid comprises urine.

13. The apparatus of claim 12, further comprising:
an alarm system for emitting an alarm when the RFID tag acts as a self-powered RFID in the presence of the fluid.

14. The apparatus of claim 13, wherein the alarm signal comprises an identifier of the RFID tag.

15. The apparatus of claim 14, wherein the alarm further comprises a location of the RFID tag.

16. The apparatus of claim 11, wherein the fluid activated battery comprises a urine activated battery.

17. A radio frequency identifier (RFID) tag, comprising:
a fluid activated battery for providing electric power to the RFID tag when a fluid is present, wherein the RFID tag is configured to:
act as a passive RFID tag when a fluid is absent; and
act as a self-powered active tag when a fluid is present.

18. The RFID tag according to claim 17, wherein the RFID tag stores information, the information comprising:
a RFID identifier and information regarding at least one of a location, a structure, an individual, or an object.

19. The RFID tag according to claim 18, wherein the information stored in the RFID tag can be read by an RFID reader when the RFID acts as a passive RFID tag, and wherein the information stored in the RFID tag can be transmitted to an RFID reader when the RFID tag acts as an active RFID tag.

20. The RFID tag according to claim 17, wherein the fluid comprises urine or water.

* * * * *